United States Patent [19]
Crickenberger et al.

[11] Patent Number: 5,728,128
[45] Date of Patent: Mar. 17, 1998

[54] FEMORAL NECK ANTEVERSION GUIDE

[75] Inventors: Dallas P. Crickenberger; Alfred A. Durham, both of Roanoke, Va.; Robert L. Daily, Germantown, Tenn.; Gregory S. Fandrich, Collierville, Tenn.; Lauralan Terrill-Grisoni, Cordova, Tenn.

[73] Assignee: Wright Medical Technology, Inc., Arlington, Tenn.

[21] Appl. No.: 795,486

[22] Filed: Feb. 11, 1997

[51] Int. Cl.⁶ .................................................. A61B 17/56
[52] U.S. Cl. ........................................... 606/97; 606/102
[58] Field of Search ............................ 606/102, 96, 97, 606/98, 89, 87, 88, 86, 62, 63, 64

[56] References Cited

U.S. PATENT DOCUMENTS

| | | | |
|---|---|---|---|
| 5,178,621 | 1/1993 | Cook et al. | 606/96 |
| 5,334,192 | 8/1994 | Behrens | 606/96 |
| 5,342,366 | 8/1994 | Whiteside et al. | 606/86 |
| 5,403,321 | 4/1995 | DiMarco | 606/96 |
| 5,478,341 | 12/1995 | Cook et al. | 606/62 |
| 5,607,431 | 3/1997 | Dudasik et al. | 606/80 |

*Primary Examiner*—Guy V. Tucker
*Attorney, Agent, or Firm*—Walker, McKenzie & Walker

[57] ABSTRACT

A femoral neck anteversion guide for use with a femur having a prepared intramedullary canal. The guide includes a radiolucent stem having a distal end for inserting into the prepared intramedullary canal; and a radiopaque angle locator wire embedded within the stem at a known angle for allowing the femoral neck angle and femoral neck anteversion to be determined.

3 Claims, 4 Drawing Sheets

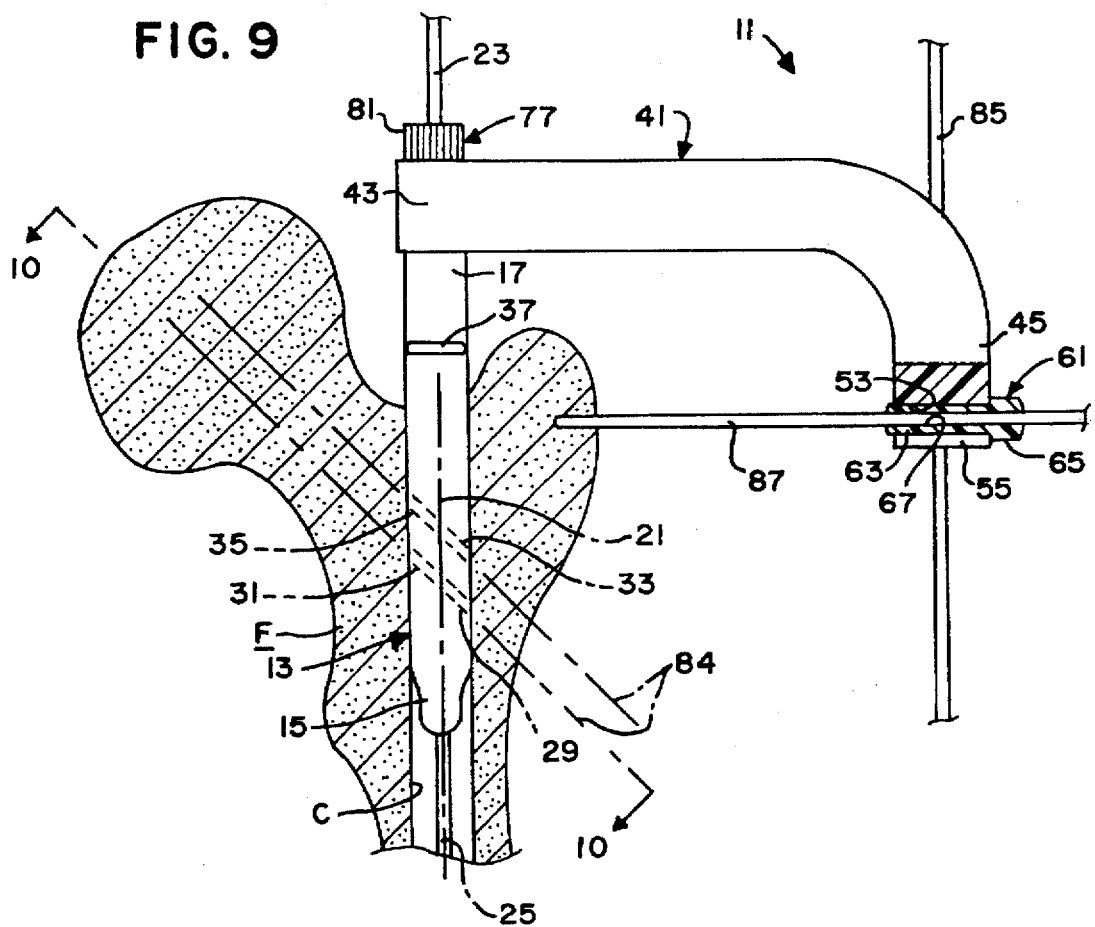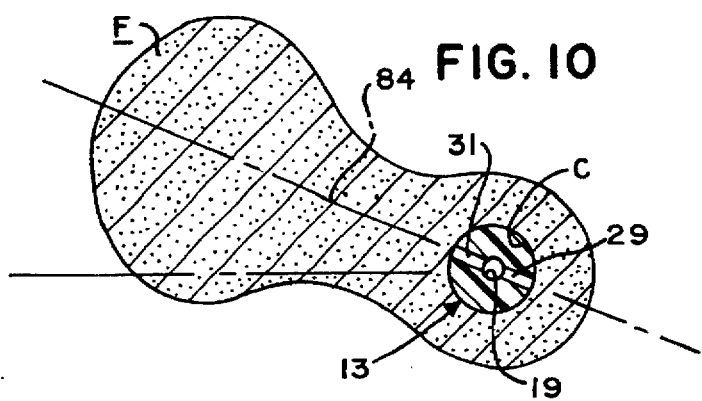

FEMORAL NECK ANTEVERSION GUIDE

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention of the Invention

The present invention relates to a surgical instrument used to help determine femoral neck angle and location prior to implantation of an implant.

2. Background Art

Various surgical devices such as proximal femoral implants, elongated femoral rods, or "nails," etc., are inserted in prepared intramedullary canals of diseased, injured, or disfigured femurs. The specific size and shape of such devices and the depth to which such devices are implanted are based, in part, on the specific femoral neck angle, femoral neck anteversion, etc. In the past, surgeons typically estimate the femoral neck angle and femoral neck anteversion during preoperative planning based on radiographs, etc.

Nothing in the known prior art discloses or suggests the present invention. More specifically, nothing in the known prior art discloses or suggests a neck anteversion guide including a radiolucent stem having a distal end for inserting into a prepared intramedullary canal of a long bone; and a radiopaque angle locator wire embedded within the stem at a known angle for allowing the neck angle and neck anteversion to be determined.

BRIEF SUMMARY OF THE INVENTION

The present invention provides a surgical instrument for used with a long bone having a head joined to a shaft by a neck to help determine femur angle and location prior to implantation of an implant. With this device, the correct implant size and angle can be chosen prior to implantation.

The neck anteversion guide of the present invention includes a radiolucent stem having a distal end for inserting into a prepared intramedullary canal of a long bone; and a radiopaque angle locator wire embedded within the stem at a known angle for allowing the neck angle and neck anteversion to be determined.

One object of the present invention is to provide an instrument that allows a surgeon to accurately size the correct implant prior to implantation.

Another object of the present invention is to provide an instrument that allows a surgeon to determine the femur neck angle, the femur neck anteversion, and the intersection of the axis of the intramedullary canal and the axis of the femur neck.

Another object of the present invention is to provide an instrument that allows a separate rigidly attached pin to be left behind as a marker and for use with any consecutive instruments.

Another object of the present invention is to provide an instrument that is entirely radiolucent except for locator pins and rings.

BRIEF DESCRIPTION OF THE SEVERAL VIEWS OF THE DRAWINGS

FIG. 6 is a sectional view of the proximal end of a right femur, showing the intramedullary canal thereof reamed to receive an intramedullary nail or the like.

FIG. 7 is a top plan view of the proximal end of a right femur, showing the intramedullary canal thereof reamed to receive an intramedullary nail or the like.

FIG. 9 is a sectional view substantially as taken on line 9—9 of FIG. 7.

FIG. 10 is a sectional view substantially as taken on line 10—10 of FIG. 9.

DETAILED DESCRIPTION OF THE INVENTION

Figure 1:
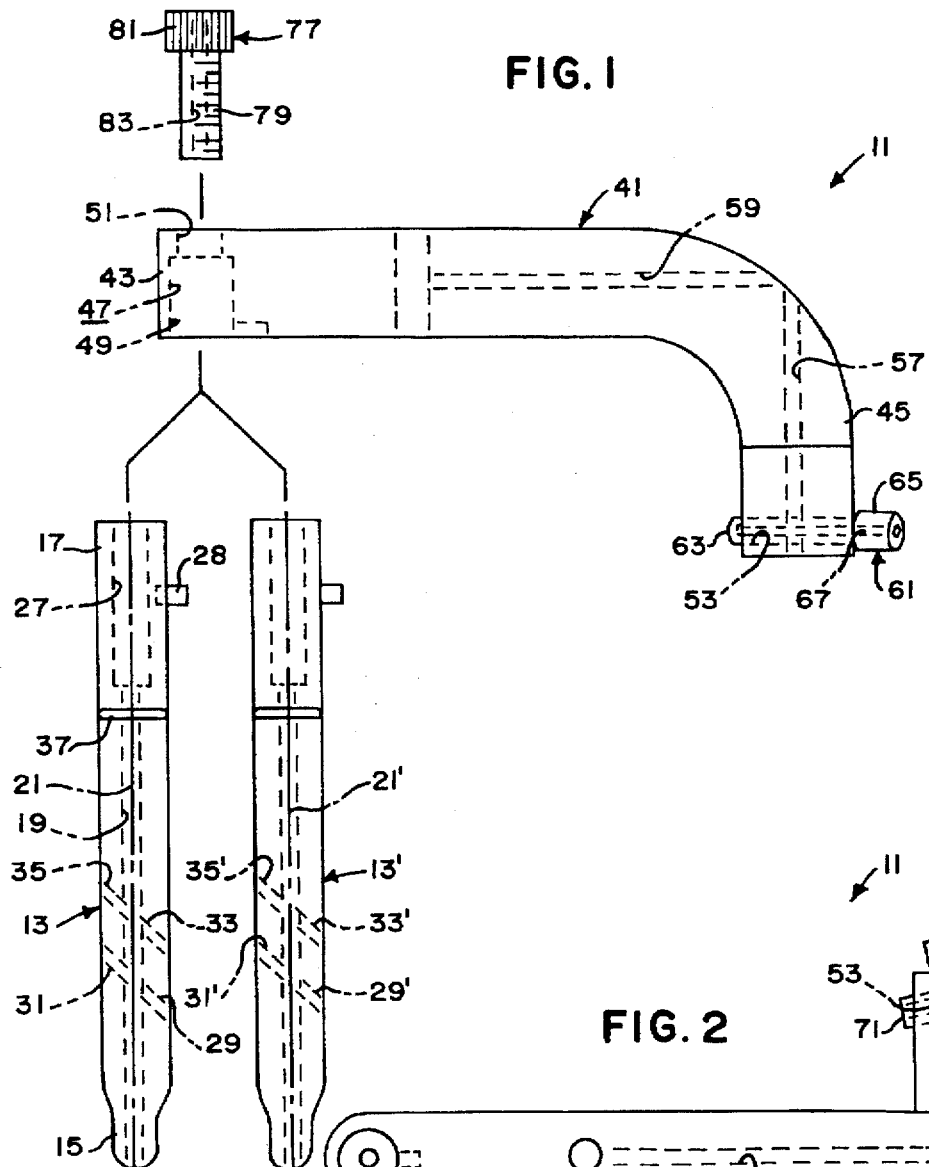
FIG. 1 is an exploded elevational view of the femoral neck anteversion guide of the present invention, showing two different size stems.
Figure 2:
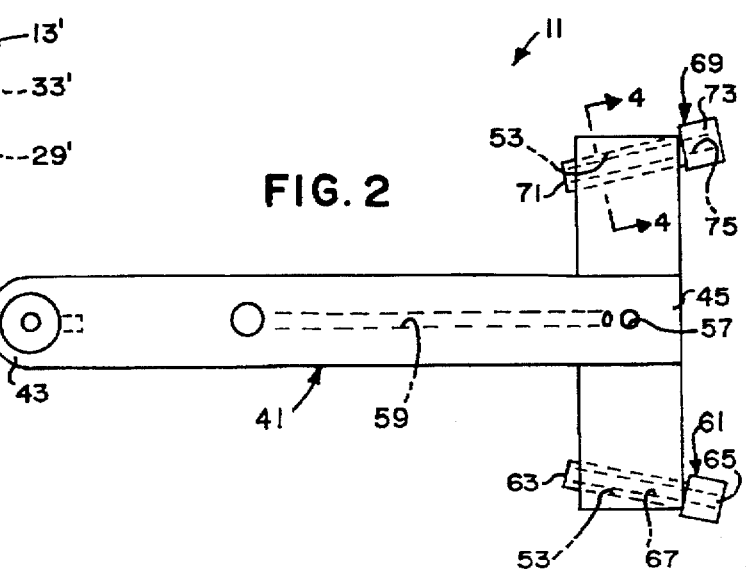
FIG. 2 is a top plan view of the femoral neck anteversion guide of the present invention.
Figure 3:
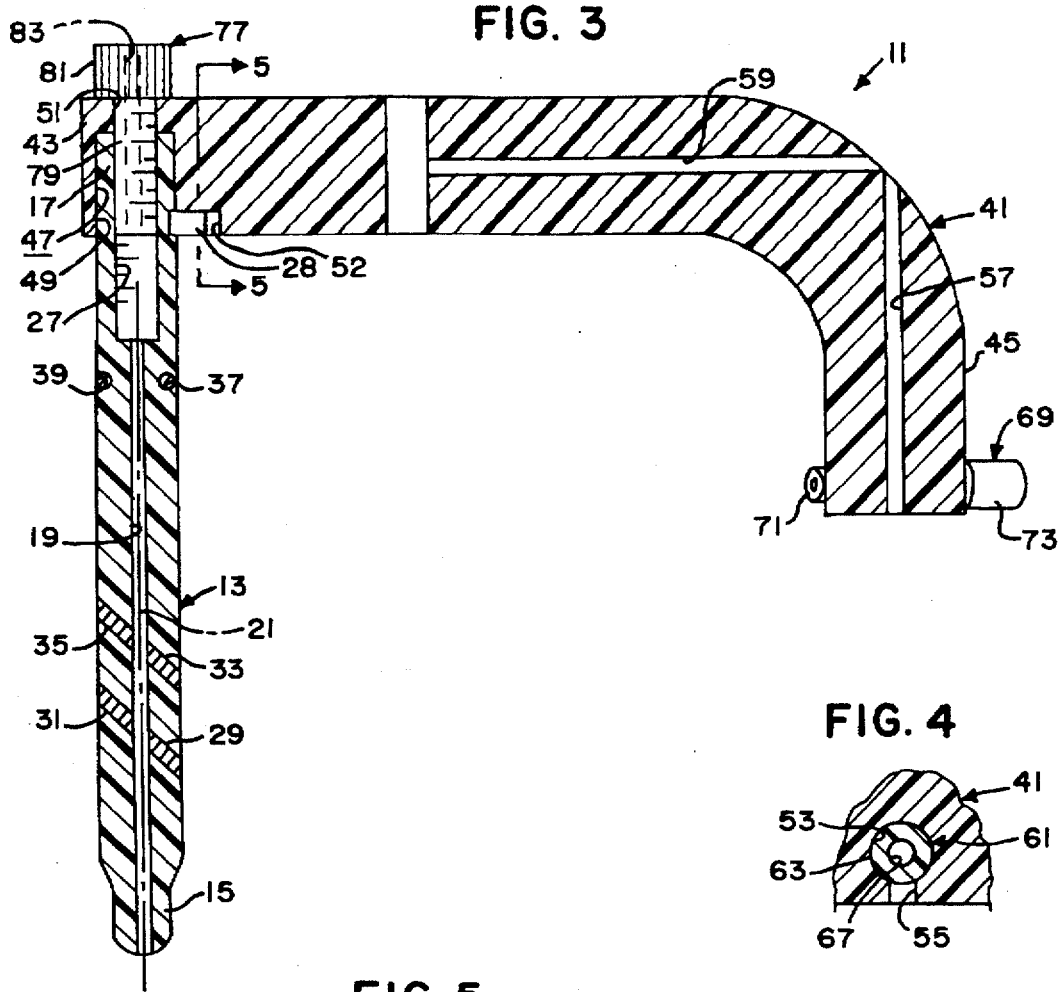
FIG. 3 is a sectional view substantially as taken on line 3—3 of FIG. 2 on a somewhat enlarged scale.
Figure 4:
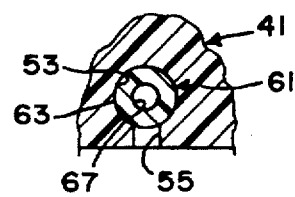
FIG. 4 is a sectional view substantially as taken on line 4—4 of FIG. 2 on a somewhat enlarged scale and with portions thereof broken away for clarity.
Figure 5:
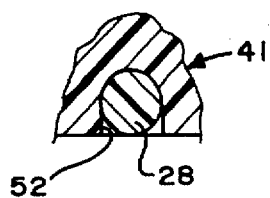
FIG. 5 is a sectional view substantially as taken on line 5—5 of FIG. 3 on a somewhat enlarged scale and with portions thereof broken away for clarity.
Figure 6:
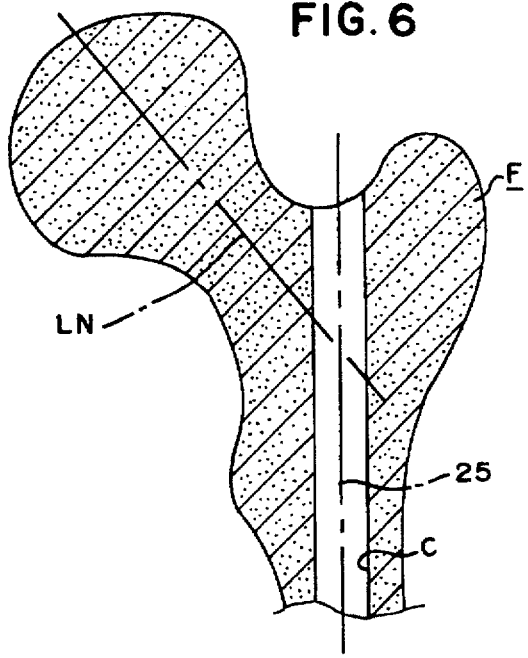
Figure 7:
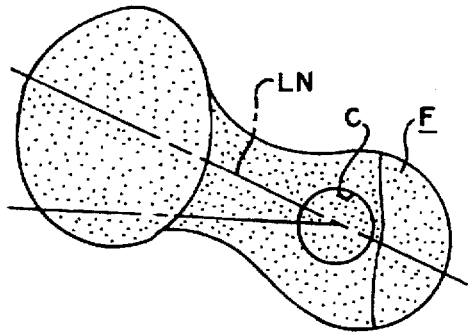
Figure 8:
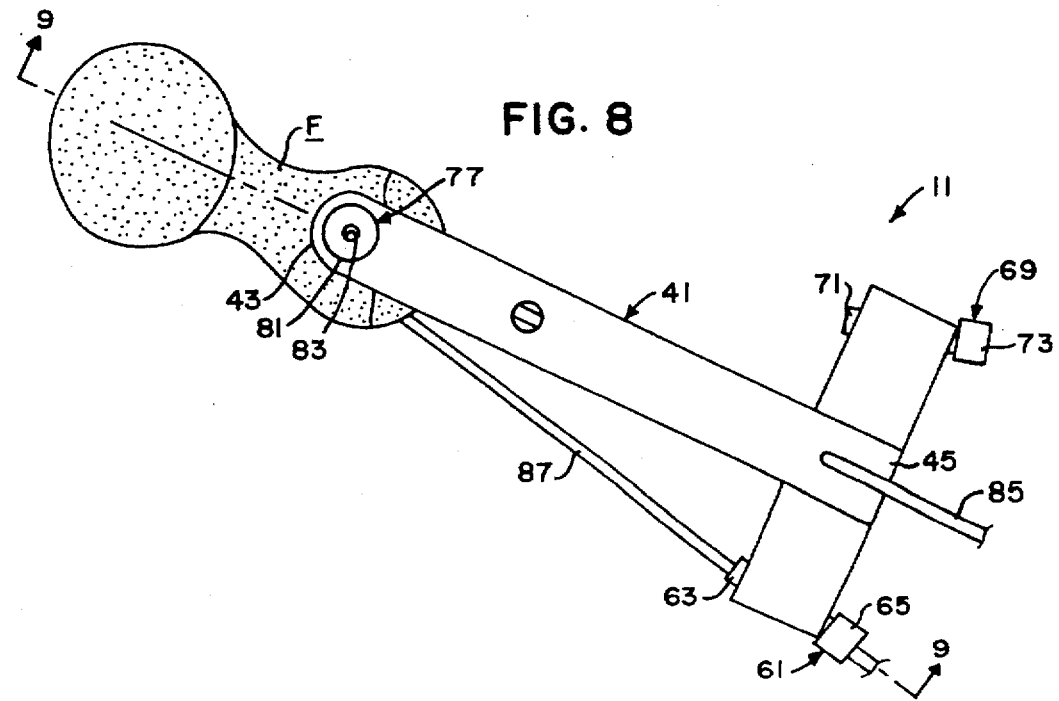
FIG. 8 is a top plan view of the proximal end of the right femur of FIG. 6, showing the femoral neck anteversion guide of the present invention inserted into the intramedullary canal thereof.

A preferred embodiment of the femoral neck anteversion guide of the present invention is shown in drawings, and identified by the numeral 11. The femoral neck anteversion guide 11 is especially designed for use with a femur F after the intramedullary canal C has been reamed or otherwise prepared to receive an intramedullary nail or other implant, etc.

The femoral neck anteversion guide 11 includes a radiolucent stem 13 having a distal end 15 for inserting into the intramedullary canal C, and a proximal end 17. The cross section shape and size is designed to fit a specific intramedullary canal C. The length of the stem 13 is preferably elongated and designed to extend into the intramedullary canal C of the femur F, past the junction of the neck N and shaft S of the femur F, a sufficient distance so as to provide a stable union between the stem 13 and femur F. The distal end 17 of the stem 13 may be tapered and rounded as clearly shown in the drawings for allowing the stem 13 to be easily inserted into the intramedullary canal C. The stem 13 preferably has a bore 19 extending completely therethrough along the longitudinal axis 21 thereof for allowing the stem 13 to be inserted over any guide pin 23 or the like that may be left attached to the femur F along the longitudinal axis 25 of the femoral shaft or the prepared intramedullary canal C for guiding the subsequent implantation of any intramedullary nail or other implant, etc. The proximal end 17 of the stem 13 preferably has an internally threaded cavity 27 therein for reasons which will hereinafter become apparent. The cavity 27 may be coaxial with the bore 19. The stem 13 is preferably constructed entirely of a radiolucent material such as by being molded or machined out of any well know radiolucent plastic or the like.

The femoral neck anteversion guide 11 preferably includes a radiolucent antirotation pin 28 for attachment to and extending outward from the outer surface the stem 13 at a location just below the proximal end 17 thereof for reasons which will hereinafter become apparent. The antirotation pin 28 is preferably constructed entirely of a radiolucent material such as by being molded or machined out of any well know radiolucent plastic or the like, and may be attached to the stem 13 in any manner now apparent to those skilled in the art such as, for example, by being press-fitted into a cavity in the outer surface of the stem 13. On the other hand, the stem 13 and antirotation pin 28 could be manufactured as a one-piece, integral unit, etc.

The femoral neck anteversion guide 11 includes at least one radiopaque angle locator means embedded within the stem 13 at a known angle, i.e., at an angle that approximates a typical femoral neck angle, for allowing the femoral neck angle and femoral neck anteversion to be determined with the aid of X-rays or the like. For example, the angle located means may be embedded within the stem 13 at an angle of 135° to the longitudinal axis 21 of the stem 13. Preferably, the femoral neck anteversion guide 11 includes a first angle locator wire 29 embedded within the stem 13 on one side of the bore 19 through the stem 13, a second angle locator wire 31 embedded within the stem 13 on the other side of the bore 19 through the stem 13 coextensive with the first angle locator wire 29 to form an extension of the first angle locator wire 29, a third angle locator wire 33 embedded within the stem 13 on one side of the bore 19 parallel to and spaced from the first angle locator wire 29, and a fourth angle locator wire 35 embedded within the stem 13 on the other side of the bore 19 coextensive with the third angle locator wire 33 to form an extension of the third angle locator wire 33.

The femoral neck anteversion guide 11 may include radiopaque height locator wire embedded within the stem 13 at an height that identifies the approximate height of the proximal end of a femoral nail, etc., when properly implanted in the femur F. The height located wire 37 preferably consist of a wire ring embedded in a groove 39 in the outer surface of the stem 13.

The femoral neck anteversion guide 11 may includes a modular set of stems 13 of different sizes, neck angle locator wires, etc. For example, as shown in FIG. 1, the femoral neck anteversion guide 11 may the stem 13 having neck angle locator wires 29, 31, 33, 35 embedded therein at an angle of 135° to the longitudinal axis 21 of the stem 13, and may include a second stem 13' identical to the stem 13 except having neck angle locator wires 29', 31', 33', 35' embedded therein at an angle of 125° to the longitudinal axis 21' of the stem 13'.

The femoral neck anteversion guide 11 includes a handle 41 having a first end 43 for attachment to the proximal end 17 of the stem 13, and a second end 45. The first end 43 of the handle 41 may have a cavity 47 extending completely therethrough with a distal end 49 sized to receive the proximal end 17 of the stem 13 and with a proximal end 51 with a cross sectional area smaller than of the proximal end 17 of the stem 13 to prevent the stem 13 from passing completely through the cavity 47. The handle 41 preferably has a slot 52 communicating with the distal end 49 of the cavity 47 for reasons which will hereinafter become apparent. The second end 45 of the handle 41 preferably has a bend that terminates distally in a tee having an angled guide hole 53 in each end of the tee. A distal slot 55 extends along the length of each guide hole 53 for reasons which will hereinafter become apparent. The handle 41 preferably has a first pin hole 57 extending through the second end 45 thereof parallel to the longitudinal axis of the cavity 47 in the first end 43 of the handle 41 (and parallel to the longitudinal axis 21 of the stem 13 and, thus, the longitudinal axis 25 of the intramedullary canal C of the femur F, when the proximal end 17 of the stem 13 is properly positioned in the cavity 47 and the distal end 15 of the stem 13 is properly positioned in the intramedullary canal C) for reasons which will hereinafter become apparent. The handle 41 preferably has a second pin hole 59 extending from the second end 45 thereof perpendicular to the longitudinal axis of the cavity 47 in the first end 43 of the handle 41 (and perpendicular to the longitudinal axis 21 of the stem 13 and, thus, the longitudinal axis 25 of the intramedullary canal C of the femur F, when the proximal end 17 of the stem 13 is properly positioned in the cavity 47 and the distal end 15 of the stem 13 is properly positioned in the intramedullary canal C) for masons which will hereinafter become apparent. The handle 41 is preferably constructed entirely of a radiolucent material such as by being molded or machined out of any well know radiolucent plastic or the like.

The femoral neck anteversion guide 11 preferably includes radiolucent first guide bushing 61 having a cylindrical body 63 for extending through one of the angled guide holes 53 through the tee of the second end 45 of the handle 41, having an enlarged head 65 on one end of the body 63, and having an aperture 67 extending completely through the body 63 and head 65 for reasons which will hereinafter become apparent. In addition, the femoral neck anteversion guide 11 preferably includes radiolucent second guide bushing 69 having a cylindrical body 71 for extending through the other angled guide holes 53 through the tee of the second end 45 of the handle 41, having an enlarged head 65 on one end 73 of the body 71, and having an aperture 75 extending completely through the body 71 and head 73 for reasons which will hereinafter become apparent. Both guide bushings 61, 69 are preferably constructed entirely of a radiolucent material such as by being molded or machined out of any well know radiolucent plastic or the like.

The femoral neck anteversion guide 11 preferably includes a radiolucent screw 77 for securely attaching the stem 13 and handle 41 to one another. The screw 77 preferably includes an externally threaded body 79 for passing through the proximal end 51 of cavity 47 and screwing into the internally threaded cavity 27 in the proximal end 17 of the stem 13 when the proximal end 17 is inserted into the distal end 49 of the cavity 47. In addition, the screw 77 preferably includes an enlarged head 81 on the proximal end of the body 79, and preferably has an aperture 83 extending completely through the body 79 and head 81 for reasons which will hereinafter become apparent. The screw 77 is preferably constructed entirely of a radiolucent material such as by being molded or machined out of any well know radiolucent plastic or the like.

The surgical technique or method of using the femoral neck anteversion guide 11 of the present invention may include typical preoperative planning to estimate proper nail or other implant size and angle, bone screw size, etc. Any typical surgical approach may be used to expose the proximal end of the femur F, etc. The intramedullary canal C of the femur F can then be prepared in any typical manner, such as by inserting a guide pin or rod into the intramedullary canal C of the femur F, and then using a cannulated reamer over the guide pin to enlarge the intramedullary canal C to the desired size and shape, etc. Once the intramedullary canal C has been reamed to the correct size, and with the guide pin remaining centered in the intramedullary canal C, the distal end 15 of the stem 13 is inserted into the intramedullary canal C. With the help of X-rays, etc., different stems 13, etc., may be tried until the angle and position of the locator wires 29, 31, 33, 35, etc., adequately match the particular femur neck angle. The longitudinal axes 84 of the locator wires 29, 31, 33, 35 should be approximately the same angle relative to the longitudinal axis 21 as that of the longitudinal axis LN of the femoral neck to the longitudinal axis 25 of the femoral shaft or intramedullary canal C. The chosen stem, for example, the stem 13, can then be attached to the handle 41 by inserting the proximal end 15 of the stem 13 into the distal end 49 of the cavity 47 with the antirotation pin 28 extending into the slot 52 to insure proper alignment of the locator wires 29, 31, 33, 35 with the handle 41, and then securing the stem 13 to the handle 41 with the screw 77 as will now be apparent to those skilled in the art (it should be noted that rather than one handle 41 and a plurality of modular stems 13, 13', etc., the present invention may include a plurality of assembled stem/handle units of different sizes, neck angles, etc.). In any event, the chosen stem, for example, the stem 13, is then positioned to the correct distal/proximal depth so that if screws were to coincide with the locator wires 29, 31, 33, 35, they would go through the femoral neck and up into the femoral head and obtain good bone purchase. The inserted stem 13 can then be rotated in the intramedullary canal C to obtain the correct anteversion angle of the locator wires 29, 31, 33, 35, again so that if screws were to coincide with the locator wires 29, 31, 33, 35, they would go through the femoral neck and up into the femoral head and obtain good bone purchase. A radiopaque pin 85 can then be inserted into one or both of the pin holes 57, 59 to act as indicators to help properly position the guide 11.

Once the surgeon is satisfied with the position of the guide 11 on the femur F, a radiopaque pin 87, such as a Steinman pin or similar device, is inserted through the appropriate guide bushing 61, 69 and embedded into the femur F so that it is rigidly attached to the femur F. The appropriate guide bushing 61, 69 depends on whether the femur F is a right or left femur. More specifically, the appropriate guide bushing 61, 69 to use should be the guide bushing 61, 69 located on the posterior side of the specific femur F. The guide 11 can then be separated from the pin 87 and removed from the femur F, leaving the pin 87 rigidly attached to the femur F, at a known location and angle to the femoral neck sot the pin 87 can bed used to hep properly position the chosen surgical device or implant in a manner as will now be apparent to those skilled in the art. To separate the guide 11 from the pin 87, the guide bushing 61, 69 through which the pin 87 extends is merely pulled or otherwise removed from the handle 41 and over the outer end of the pin 87. The guide 11 can then be lifted up from the femur F, causing the pin 87 to pass through the distal slot 55 in the handle 41 as will now be apparent to those skilled in the art.

Although the present invention has been described and illustrated with respect to a preferred embodiment and a preferred use therefor, it is not to be so limited since modifications and changes can be made therein which are within the full intended scope of the invention.

We claim:

1. A neck anteversion guide for use with a long bone having a prepared intramedullary canal, the guide comprising:

(a) a radiolucent stem having a distal end for inserting into the prepared intramedullary canal, and having a proximal end; and (b) radiopaque angle locator means embedded within the stem at a known angle for allowing the neck angle and neck anteversion to be determined.

2. The neck anteversion guide of claim 1 in which is included a radiolucent handle having a first end for attachment to the proximal end of the stem, and having a second end.

3. The neck anteversion guide of claim 2 in which is included a radiolucent guide bushing attached to the second end of the handle for allowing a guide pin to be inserted into the long bone at a known location.

\* \* \* \* \*